| (12) | United States Patent | (10) Patent No.: | US 7,581,264 B2 |
|---|---|---|---|
| | Mangiardi | (45) Date of Patent: | Sep. 1, 2009 |

(54) RE-DESIGN OF OPERATING ROOM TABLES

(75) Inventor: John R. Mangiardi, Greenwich, CT (US)

(73) Assignee: Optimus Services, LLC, Greenwich, CT (US)

( * ) Notice: Subject to any disclaimer, the term of this patent is extended or adjusted under 35 U.S.C. 154(b) by 0 days.

(21) Appl. No.: 11/996,040

(22) PCT Filed: Jul. 20, 2006

(86) PCT No.: PCT/US2006/028233

§ 371 (c)(1),
(2), (4) Date: Feb. 6, 2008

(87) PCT Pub. No.: WO2007/012044

PCT Pub. Date: Jan. 25, 2007

(65) Prior Publication Data

US 2008/0216241 A1    Sep. 11, 2008

Related U.S. Application Data

(60) Provisional application No. 60/701,106, filed on Jul. 20, 2005.

(51) Int. Cl.
*A61G 13/02* (2006.01)

(52) U.S. Cl. .................................... 5/611; 5/600; 5/616
(58) Field of Classification Search ............. 5/600–602, 5/607–618
See application file for complete search history.

(56) References Cited

U.S. PATENT DOCUMENTS

| 2,217,783 | A | | 10/1940 | Bell | |
|---|---|---|---|---|---|
| 3,362,704 | A | * | 1/1968 | Pilz .............................. | 5/618 |
| 5,991,947 | A | * | 11/1999 | Lavin et al. .................... | 5/600 |
| 6,155,260 | A | | 12/2000 | Lavin et al. | |
| 6,553,588 | B2 | * | 4/2003 | Hensley et al. ................. | 5/600 |

* cited by examiner

*Primary Examiner*—Alexander Grosz
(74) *Attorney, Agent, or Firm*—Hunton & Williams LLP

(57) ABSTRACT

A patient table, modified with a fixed-base design thereby allowing for heavy patients, providing tilting and cantilevering capabilities, table top extension (i.e. providing head to toe coverage), and overall stability, is described. The operating room table re-design includes incorporation of utility sources into the architecture of the table, so that utilities, such as wiring, vacuum, and gas hoses, arise from the table itself. The source of all utilities to the table (as opposed to those emanating from the table) may come from an underground connection. Further, the table is interchangeable with tables customized for a specific procedure.

10 Claims, 3 Drawing Sheets

RE-DESIGN OF OPERATING ROOM TABLES

CROSS-REFERENCE TO RELATED APPLICATIONS

This application claims the priority benefit of PCT/US06/028233 filed on Jul. 20, 2006 and from provisional patent application U.S. Ser. No. 60/701,106, filed on Jul. 20, 2005 by the present inventor. The contents of PCT/US06/028233 and U.S. Ser No. 60/701,106 are expressly incorporated herein by reference thereto.

The following references are hereby explicitly incorporated by reference thereto:
U.S. Pat. No. 4,101,120
U.S. Pat. No. 5,048,071
U.S. Pat. No. 5,231,719
U.S. Pat. No. 6,170,102

BACKGROUND OF THE INVENTION

1. Field of Invention

The present invention generally relates to an apparatus for supporting patients during medical procedures and, more specifically, to surgical tables providing improved access to utilities such as gas, power, and liquids.

2. Background of the Invention

Conventional surgical tables often include a flat patient support and a lower base for holding the patient support a predetermined distance from the floor. The base of conventional surgical tables commonly includes control apparatus for tilting the flat patient support through a range of orientations to facilitate performance of certain surgical procedures. As such, it is clear that of the many functions an operating room table must provide, it must allow access to sites on a patient wherein a surgical procedure is to occur. While it is known that surgical tables may provide powered or manually actuated means for rotating the patient support platform, or even tilting and cantilevering the platform, the exigencies of a certain medical procedure may require that the support platform itself be uniquely customized for the procedure at hand. The capability of rotation, tilting, and other translational movements is insufficient to provide the necessary surgical access in all cases. For example, an obstrometric table has a unique design layout from a table used in arthroscopic surgery. As a result, modem operating rooms utilize numerous surgical tables; however, operating room floor space is typically scarce. As a result, it is a disadvantage to provide numerous operating room tables, each configured for a particular type of procedure.

One improvement shown in the prior art, the "Operating Table with Removable Patient Support Surface Means" in U.S. Pat. No. 5,231,719 by Schnelle, describes an operating table in which the patient support means may be removed, leaving the support column, to allow easy repositioning of the support column. The art does not describe the use of an interchangeable set of tables, customized for specific surgical procedures. Further, the table described, while positionable, must be actuated manually. Because manual positioning is time-consuming, it is dangerous, as a medical procedure emergency may require quick access to a particular site.

Another deficiency in modern surgical tables is the lack of convenient access to utilities required for a surgical procedure. For example, during a typical procedure, a surgeon might require a scavenging connection, such as to provide suction, or a gas line, such as to provide oxygen. Of the many utilities required comes the related safety issue that the presence of these numerous cables, hoses, and wires causes. A surgeon or attendant who trips on a cable can cause injury to the surgeon and to the patient. Further, a table, which allows positioning to provide access to a patient, is severely limited to further adjustment during a procedure as cables, wires, and hoses impose limits on the ability of a surgeon to reposition a patient.

Because of these deficiencies in the art, an operating room table and support column combination that would allow powered repositioning of a patient support means while connected to a multitude of utility connections originating from the table itself would be of benefit. Further, an operating room table and support column combination in which the operating room table is removable and allows attachment of customized patient support means would be of further benefit.

SUMMARY OF THE INVENTION

A patient table, modified with a fixed-base design thereby allowing for heavier patients, greater tilting and cantilevering capabilities, greater table top extension (i.e. providing head to toe coverage), and overall stability, is described. The operating room table re-design includes incorporation of utility sources into the architecture of the table, so that utilities, such as wiring, vacuum, and gas hoses, arise from the table itself, rather than tracking over the operating room floor. The source of all utilities to the table (as opposed to those emanating from the table) may come from an underground connection. Further, the table is interchangeable with tables customized for a specific procedure.

In a typical use, the patient table is positioned next to a support arm and fixed into place by a rod inserted through a support arm anchor and an anchor on the table or by other means. The rod, in one embodiment, may then be bolted. Alternatively, the patient table is laid on top of a support structure on the support arm or column. By resting on the support structure, a lock is actuated which stably secures the table into place. During either of the above processes, or other interlocking means contemplated by this invention, the utility lines will also be connected as between the support arm and the table. A simple receptacle to connector interface may be used or the utility lines may be connected by docking of the table during connection of the table with the support structure, i.e. support arm, cylinder, or surface. The table may then be positioned by powered means using structures known in the art. For example, hinges attached to arms connected by pivots are powered by an actuator that then provides the ability to position the table. In addition, the base of the support structure, i.e. the area below the upper support cylinder or arms, is capable of rotation along the vertical axis, preferably 180 degrees in either direction, thereby providing 360 degrees of motion. The rotation is preferably provided by hydraulic, powered means, such as by placing the support structure onto a rotating pedestal which itself rests on a bushing. The entire structure is anchored into the ground, preferably to a steel plate that runs along the sub-flooring and is anchored into the sub-flooring materials. All utility connections will run from the subflooring into the support structure and finally into the tabletop.

As operating room procedures change, the table may be interchanged with an alternative table provided it is adapted to dock with the support structure and support structure utilities. The table is further adapted to provide utility connections at various points along the table, thereby allowing easy, unobstructed access to critical utilities.

In keeping with the present invention, it is an object of the invention to provide an operating room table and support column that allows the patient support means to be separated from the support column, and to be replaced with an alternative patient support means adapted for the surgical procedure at hand.

It is an object of this invention that the support column is adapted to allow positioning of the table. As such, the support column may, for example, consist of arms, joined at pivots, and moved by powered braces to provide positioning of the table. In addition, the base of the column may be rotatable.

It is yet another object of the invention to provide an operating room table and support column in which the above patient support means is further adapted to provide receptacles and connectors for a variety of utilities used in medical procedures with the said utilities sourced from within the table through the support column and then from an outside source.

It is still another object of the invention to provide an operating room table and support column capable of supporting heavy patients and attached equipment.

At least one of the above objects is met in whole or in part by the present invention. Further objects are apparent after consideration of the following description and claims.

BRIEF DESCRIPTION OF THE DRAWINGS

The present invention can best be understood in connection with the accompanying drawings. It is noted that the invention is not limited to the precise embodiments shown in drawings, in which.

BRIEF DESCRIPTION OF REFERENCE NUMERALS

100 Surgical Table and Support Column; 102 Surgical Bed and Pads; 104 Top Frame; 106 Outlet/Inlet; 108 Utility Connection; 110 Utility Connection; 112 Raised Position; 114 Lowered Position; 116 Pivot; 118 Upper Support Rib; 120 Arm; 122 Pivot; 124 Floor; 126 Pivot; 128 Brace; 130 Arm; 132 Brace; 134 Utility Lines; 136 Housing; 138 Rotation Base; 140 Support Anchor; 150 Patient Support Means; 152 Hinge, Latch; 154 Utility Box; 156 Utility Access Point; 158 Lower Support Column; 160 Upper Support Column; 162 Actuator, Piston; 164 Turntable, Bushing; 166 Support Block; 168 Floor; 170 Utility Wires, Cables, Hoses; 172 Anchor; 200 Utility Junction; 202 Utility Junction Means; 204 Support-Column Junction Support, Back-Grid; 206 Support-Column Junction Support, Front-Grid; 208 Recessed Notch; 210 Utility Receptacle; 212 Rod Housing; 214 Anchor; 216 Table Junction Support, Grid; 218 Connector Body; 220 Utility Connector/Adaptor; 222 Utility Cable 224 Bolt and Rod Assembly, Support Column; 226 Bolt and Rod Assembly, Table; 228 Anchor Plate, Support Column; 230 Anchor Plate, Table; 232 Support Structure; 240 Threaded Rod

DETAILED DESCRIPTION OF THE INVENTION

Figure 1:
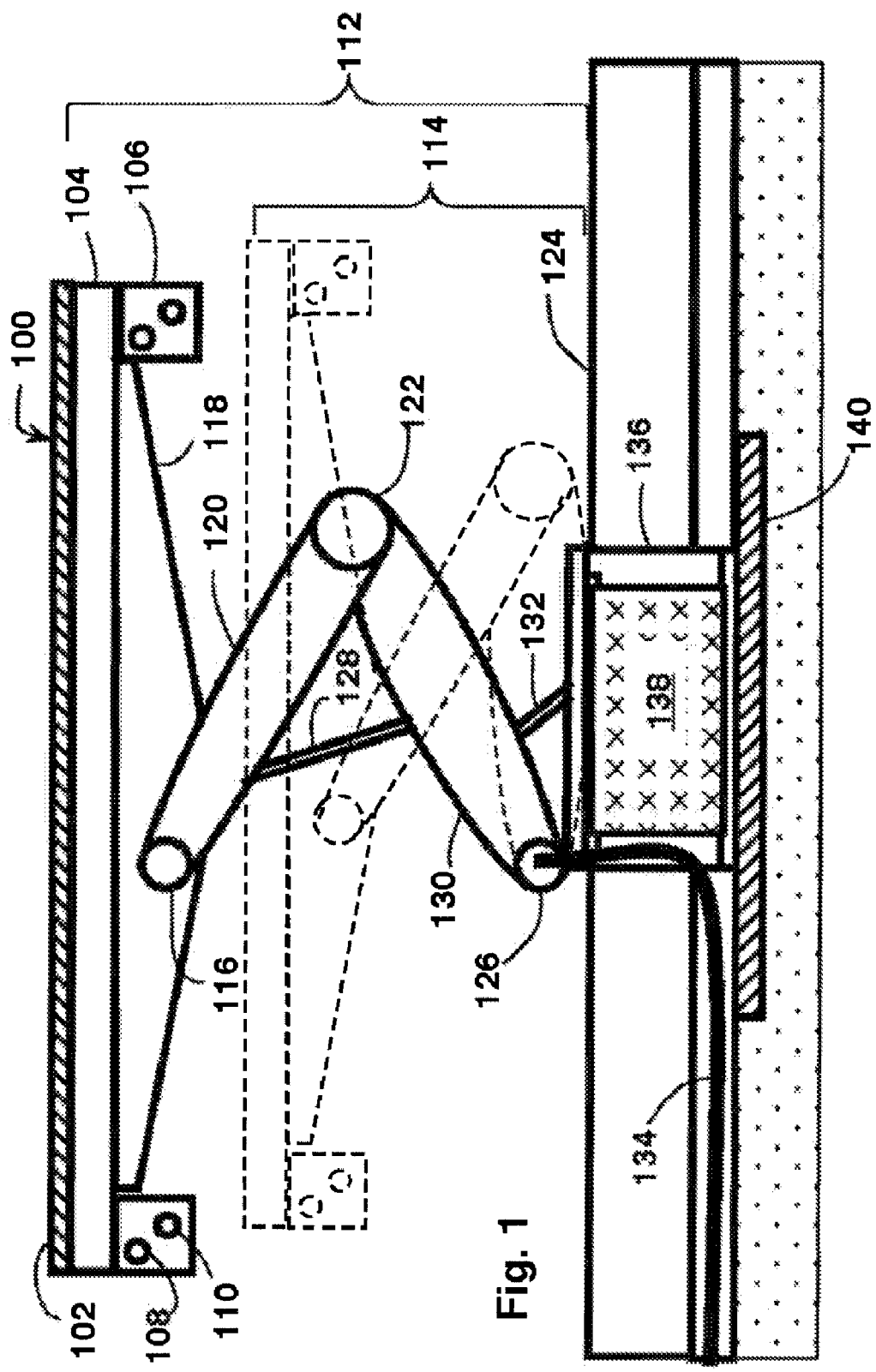
FIG. 1 is a side elevation view of a patient table in accordance with the invention.

FIG. 1 is a side view of surgical table 100 in raised 112 position or in lowered position 114 above floor 124 of the operating room. Housing 136 is provided for surgical table 100. Surgical bed 102 is solidly attached to a strong sub-base, such as, for example, steel plate 140, which is bolted or otherwise attached into the sub floor (below 124), made from, for example, concrete. Powered braces 128 and 132 are used to raise and lower top frame 104 with pads 102 via arms 120 and 130 riding in pivots 116, 122, and 126. Robustly built to support heavy patients, such as, for example, a 550-pound patient, table 100 has upper support rib 118; and the tabletop of table 100 can cantilever, rotate, and slide. All utilities, such as power, vacuum, electrical, and gas, are fed through the housing 136 as illustrated by lines 134. These lines are carried to outlet/inlet 106 at either head or toe ends. If necessary, utility outlet/inlets 106 have utility connections 108 and 110 and are accessible at either end of table 100. Surgical table 100 can be rotated 360 degrees about rotation base 138 within pod housing 136.

Figure 2:
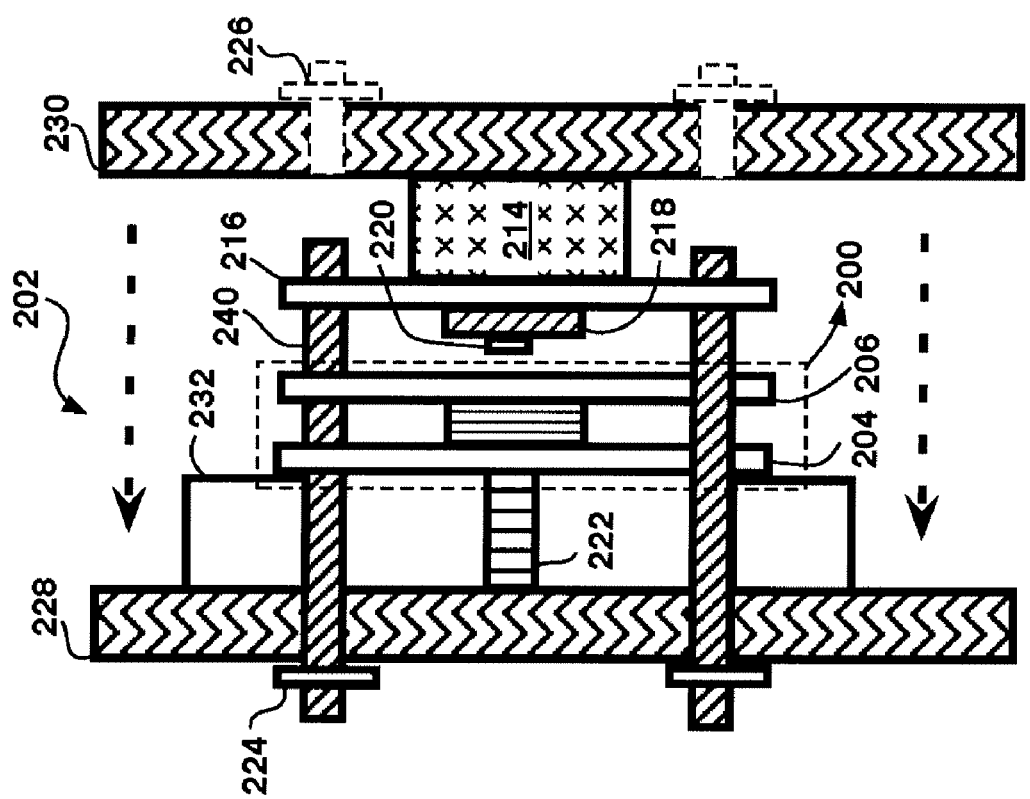
FIG. 2 is a side view of one possible patient table, support-column interfacing means.

In FIG. 2, a possible means for allowing the patient support table to be interchanged while providing a connection for utilities sourced from the support column is shown. Structure 200 encompasses a pair of support sheets or grids 204 and 206 with rod housings 212 (dotted arrow showing the pathway of a rod 240 (not shown)). The rod housings may be threaded to integrate with a threaded rod and thereby provide additional stability. Utility receptacle 210 is also shown in a recessed notch 208 thereby allowing a connection to dock within the notch 208 and hence with utility receptacle 210. The housings 212 allow the rod 240 (not shown) to enter and anchor with an anchoring means on the support column. Attached to rod 240 or anchored to rod 240 may be a connector for receptacle 210 and the patient table 100. This can be seen more clearly in FIG. 3.

Figure 3:
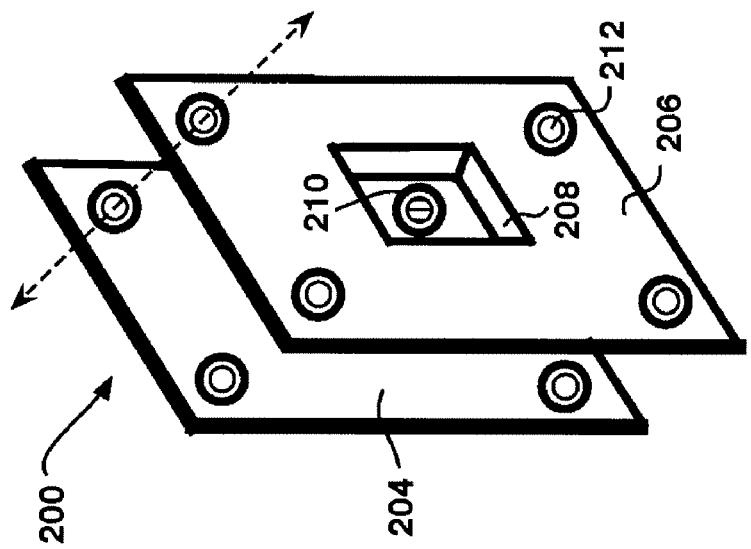
FIG. 3 is a detail view of the support-column interface receptacle.

In FIG. 3, a support column/patient table junction means 202 is shown with the table anchor 230, grid/sheet 216 sandwiched between support anchor 214 and connector housing 218, itself providing adaptor/connector 220, being inserted onto the rods already secured onto the support column anchor 228 at 224. Rods such as rod 240 inserted through grids/sheets 204, 206, and 216 provide a stable interface between the support column and the table. As can be seen, the rods may be bolted as in rod/bolt 224 and in the shadowed rod/bolt 226. Utilities sourced from the support column may be fed into the receptacle by cabling 222. Further support may be provided by additional structures such as 232.

Figure 4:
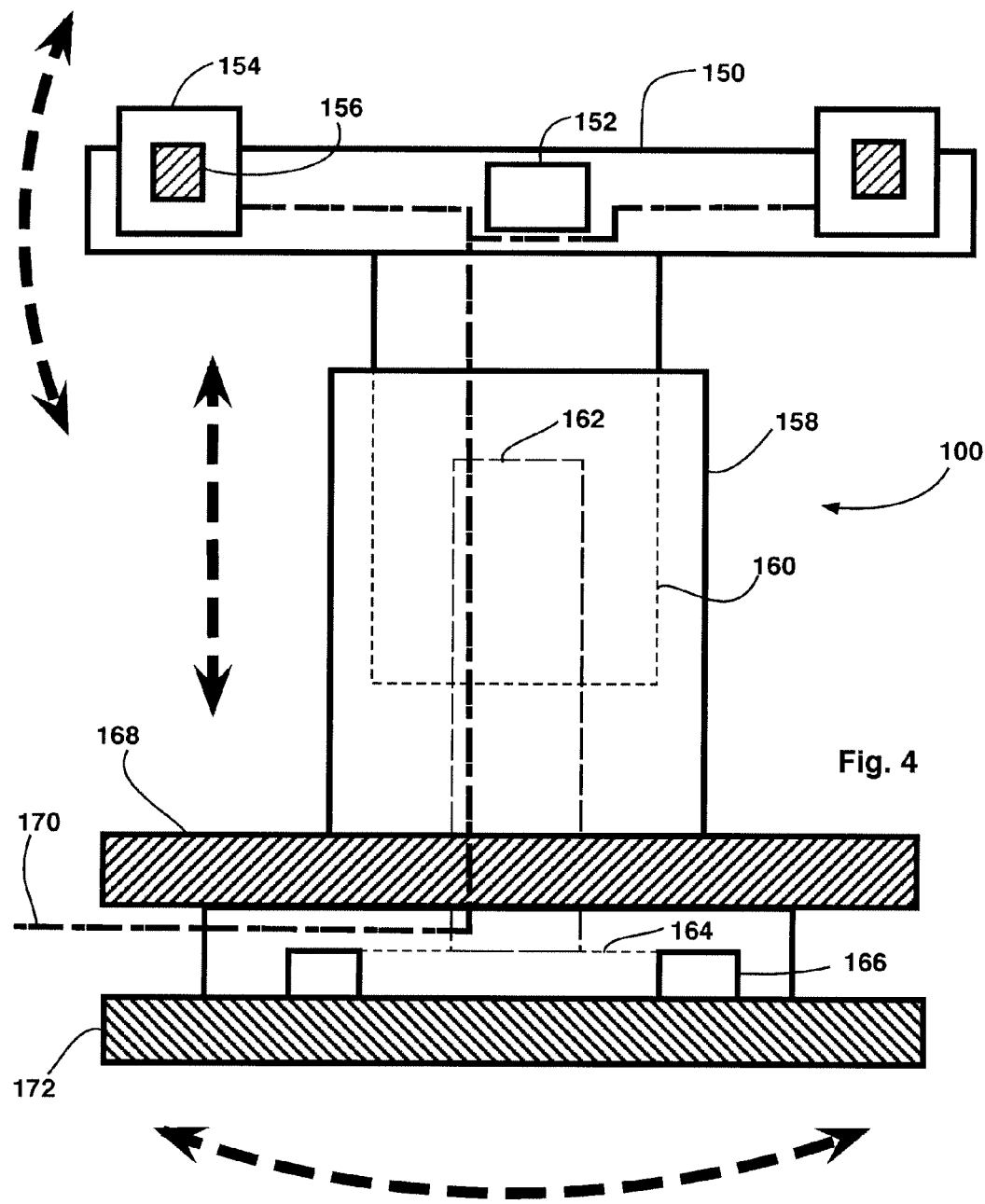
FIG. 4 is a side cross-sectional view of an additional embodiment of this invention showing a table with alternate support means.

FIG. 4 shows an alternative embodiment of the surgical table 4 shown in FIG. 1. In this conception of table 100, patient table support means 150 is hinged at point 152, thereby allowing tilting of the table. Utility box 154 (which can be disposed alone or with other boxes anywhere on table 150) provides receptacles/connections 156. All utility lines, connections, wires, cables 170 are fed to the box 154 from within support means 150, support columns 158 and 160, and underneath floor 168. The table is vertically displaceable by movement of column 160 past 158 by an actuator/piston combination 162. The support column rests on, by support from 162, bushing/turntable 164 mounted within block 166 thereby allowing rotation. The entire table, column combination is stably anchored by anchor 172, which is affixed to materials beneath floor 168. Patient table support means 150 may be removed at the hinge point or additionally at other points of joining to the support column, thereby allowing like patient table support means to be reattached, which are specially configured for particular surgical procedures. The patient table support means share the feature of having utility boxes 154 with internal sourcing of utilities.

In the foregoing description, certain terms and visual depictions are used to illustrate the preferred embodiment.

However, no unnecessary limitations are to be construed by the terms used or illustrations depicted, beyond what is shown in the prior art, since the terms and illustrations are exemplary only, and are not meant to limit the scope of the present invention. It is further known that other modifications may be made to the present invention, without departing the scope of the invention, as noted in the appended claims.

I claim:

1. A medical procedure and operating table (100), comprising:
   a support column (158, 160), said support column (158, 160) adapted to allow an attached patient support surface (150) to be positioned;
   said patient support surface (150) releasably mounted on said support column (158, 160) and adapted to provide utilities emanating from within said patient support surface, said utilities entering said patient support surface (150) from said support column (158, 160), said utilities entering (134, 170) said support column (158, 160) from a point underneath a floor (124, 168).

2. The table (100) in claim 1 in which said support column (158, 160) comprises arms (120, 130) mounted on pivots (116, 122, 126) and actuated by powered braces (128, 132).

3. The table (100) claim 2 in which said powered braces (128, 132) are actuated (162) from a motor, an electro-mechanical generator, an electro-hydraulic pump, or an electro-pneumatic pump.

4. The table (100) in claim 1 in which said utilities are provided by receptacles, connectors, or a combination of receptacles and connectors (108, 110, 156).

5. The table (100) in claim 4 in which gas or scavenging utilities are provided by means of connection with a universal adaptor.

6. The table (100) in claim 5 in which said patient support means (150) docks into or onto said support column and said utilities sourced from said support column (158, 160) is thereby sourced into said patient support surface (102).

7. The table (100) in claim 1 in which said patient support means (150) docks into or onto said support column (158, 160) and said utilities sourced from said support column (158, 160) is thereby sourced into said patient support surface (150).

8. The table (100) in claim 7 in which said support column (158, 160) is mounted permanently into said floor (124, 168) by anchoring to said floor (124, 168).

9. The table (100) in claim 1 wherein said positioning is by rotation, by vertical displacement from said floor (168), and by cantilevering with respect to said floor (124, 168).

10. The table (100) in claim 1 in which said support column (158, 160) is mounted permanently into said floor by anchoring to said floor (124, 168).

* * * * *